(12) United States Patent
Agashe et al.

(10) Patent No.: US 7,643,858 B2
(45) Date of Patent: Jan. 5, 2010

(54) SYSTEM AND METHOD FOR DETECTION OF BRAIN EDEMA USING SPECTROPHOTOMETRY

(75) Inventors: Geeta Agashe, Freemont, CA (US); Martin P. Debreczeny, Danville, CA (US)

(73) Assignee: Nellcor Puritan Bennett LLC, Boulder, CO (US)

( * ) Notice: Subject to any disclaimer, the term of this patent is extended or adjusted under 35 U.S.C. 154(b) by 251 days.

(21) Appl. No.: 11/529,024

(22) Filed: Sep. 28, 2006

(65) Prior Publication Data

US 2008/0081975 A1   Apr. 3, 2008

(51) Int. Cl.
*A61B 5/00* (2006.01)

(52) U.S. Cl. ................................ 600/310; 600/561
(58) Field of Classification Search .............. 600/561, 600/473, 475
See application file for complete search history.

(56) References Cited

U.S. PATENT DOCUMENTS

| | | |
|---|---|---|
| 3,998,550 A | 12/1976 | Konishi et al. |
| 4,066,068 A | 1/1978 | Nilsson et al. |
| 4,364,008 A | 12/1982 | Jacques |
| 4,711,244 A | 12/1987 | Kuzara |
| 4,723,554 A | 2/1988 | Oman et al. |
| 4,805,623 A | 2/1989 | Jobsis |
| 4,850,365 A | 7/1989 | Rosenthal |
| 4,860,753 A | 8/1989 | Amerena |
| 4,883,055 A | 11/1989 | Merrick |
| 4,907,594 A | 3/1990 | Muz |
| 5,057,695 A | 10/1991 | Hirao et al. |
| 5,086,781 A | 2/1992 | Bookspan |
| 5,111,817 A | 5/1992 | Clark et al. |
| 5,146,091 A | 9/1992 | Knudson |
| 5,224,478 A | 7/1993 | Sakai et al. |
| 5,277,181 A | 1/1994 | Mendelson et al. |
| 5,279,295 A | 1/1994 | Martens et al. |
| 5,282,467 A | 2/1994 | Piantadosi et al. |
| 5,337,745 A | 8/1994 | Benaron |

(Continued)

FOREIGN PATENT DOCUMENTS

CA   2353007 A1   6/2000

(Continued)

OTHER PUBLICATIONS

"Noninvasive Early Detection of Brain Edema in Mice by Near-Infrared Light Scattering," Jay R. Thiagarajah, Marios C. Papadopoulos, and A. S. Verkman; Journal of Neuroscience Research 80:293-299 (2005).*

(Continued)

*Primary Examiner*—Max Hindenburg
*Assistant Examiner*—Michael C. Stout
(74) *Attorney, Agent, or Firm*—Fletcher Yoder

(57) ABSTRACT

Embodiments of the present invention relate to a system and method of detecting or monitoring brain edema in a patient. One embodiment of the present invention includes emitting a first light into the patient's brain tissue at a first wavelength, emitting a second light into the patient's brain tissue at a second wavelength, detecting the first and second lights after dispersion by the brain tissue at a detector, and determining an amount of water proximate the brain tissue based on the detected first and second lights.

16 Claims, 4 Drawing Sheets

U.S. PATENT DOCUMENTS

| | | |
|---|---|---|
| 5,337,937 A | 8/1994 | Remiszewski et al. |
| 5,348,003 A | 9/1994 | Caro |
| 5,348,004 A | 9/1994 | Hollub |
| 5,355,880 A | 10/1994 | Thomas et al. |
| 5,377,674 A | 1/1995 | Kuestner |
| 5,499,627 A | 3/1996 | Steuer et al. |
| 5,527,822 A | 6/1996 | Scheinen |
| 5,615,689 A | 4/1997 | Kotler |
| 5,687,721 A | 11/1997 | Kuhls |
| 5,701,902 A | 12/1997 | Vari et al. |
| 5,720,284 A | 2/1998 | Aoyagi et al. |
| 5,735,284 A | 4/1998 | Tsoglin et al. |
| 5,747,789 A | 5/1998 | Godik |
| 5,755,672 A | 5/1998 | Arai et al. |
| 5,788,643 A | 8/1998 | Feldman |
| 5,803,908 A | 9/1998 | Steuer et al. |
| 5,827,181 A | 10/1998 | Dias et al. |
| 5,833,602 A | 11/1998 | Osemwota |
| 5,853,364 A | 12/1998 | Baker, Jr. et al. |
| 5,860,919 A | 1/1999 | Kiani-Azarbayjany et al. |
| 5,906,582 A | 5/1999 | Kondo et al. |
| 6,064,898 A | 5/2000 | Aldrich |
| 6,125,297 A | 9/2000 | Siconolfi |
| 6,149,591 A | 11/2000 | Henderson et al. |
| 6,178,342 B1 | 1/2001 | Thompson et al. |
| 6,216,022 B1 * | 4/2001 | Tyrrell et al. ................ 600/310 |
| 6,222,189 B1 | 4/2001 | Misner et al. |
| 6,246,894 B1 | 6/2001 | Steuer et al. |
| 6,280,396 B1 | 8/2001 | Clark |
| 6,336,044 B1 | 1/2002 | Ghiassi et al. |
| 6,370,426 B1 | 4/2002 | Campbell et al. |
| 6,400,971 B1 | 6/2002 | Finarov et al. |
| 6,402,690 B1 | 6/2002 | Rhee et al. |
| 6,406,427 B1 | 6/2002 | Williams et al. |
| 6,442,408 B1 | 8/2002 | Wenzel et al. |
| 6,466,807 B1 | 10/2002 | Dobson et al. |
| 6,488,677 B1 | 12/2002 | Bowman et al. |
| 6,512,936 B1 | 1/2003 | Monfre et al. |
| 6,591,122 B2 | 7/2003 | Schmitt |
| 6,592,574 B1 | 7/2003 | Shimmick et al. |
| 6,600,946 B1 | 7/2003 | Rice |
| 6,606,509 B2 | 8/2003 | Schmitt |
| 6,615,064 B1 | 9/2003 | Aldrich |
| 6,635,491 B1 | 10/2003 | Khalil et al. |
| 6,636,759 B2 | 10/2003 | Robinson |
| 6,643,543 B2 | 11/2003 | Takehara et al. |
| 6,654,620 B2 | 11/2003 | Wu et al. |
| 6,668,181 B2 * | 12/2003 | Wenzel et al. ................ 600/310 |
| 6,675,029 B2 | 1/2004 | Monfre et al. |
| 6,687,519 B2 | 2/2004 | Steuer et al. |
| 6,777,240 B2 | 8/2004 | Hazen et al. |
| 6,796,941 B2 | 9/2004 | Williams et al. |
| 6,816,743 B2 * | 11/2004 | Moreno et al. ................ 600/473 |
| 6,849,046 B1 | 2/2005 | Eyal-Bickels et al. |
| 6,909,912 B2 | 6/2005 | Melker |
| 6,934,570 B2 | 8/2005 | Kiani et al. |
| 6,950,687 B2 | 9/2005 | Al-Ali |
| 6,950,699 B1 | 9/2005 | Manwaring et al. |
| 6,979,812 B2 | 12/2005 | Al-Ali |
| 6,985,763 B2 | 1/2006 | Boas et al. |
| 6,985,764 B2 | 1/2006 | Mason et al. |
| 6,993,371 B2 | 1/2006 | Kiani et al. |
| 7,024,235 B2 | 4/2006 | Melker et al. |
| 7,039,449 B2 | 5/2006 | Al-Ali |
| 7,047,054 B2 | 5/2006 | Benni |
| 7,067,893 B2 | 6/2006 | Mills et al. |
| 7,072,701 B2 | 7/2006 | Chen et al. |
| 7,096,054 B2 | 8/2006 | Abdul-Hafiz et al. |
| 7,127,278 B2 | 10/2006 | Melker et al. |
| 7,130,672 B2 | 10/2006 | Pewzner et al. |
| 7,221,969 B2 | 5/2007 | Stoddart et al. |
| 7,236,811 B2 | 6/2007 | Schmitt |
| 7,239,902 B2 | 7/2007 | Schmitt et al. |
| 7,251,518 B2 | 7/2007 | Herrmann |
| 7,272,425 B2 | 9/2007 | Al-Ali et al. |
| 7,277,741 B2 | 10/2007 | Debreczeny et al. |
| 7,280,858 B2 | 10/2007 | Al-Ali et al. |
| 7,289,837 B2 | 10/2007 | Mannheimer et al. |
| 7,313,427 B2 | 12/2007 | Benni |
| 7,332,784 B2 | 2/2008 | Mills et al. |
| 7,340,287 B2 | 3/2008 | Mason et al. |
| 7,349,726 B2 | 3/2008 | Casciani et al. |
| 7,356,365 B2 | 4/2008 | Schurman |
| 7,376,454 B2 | 5/2008 | Casciani et al. |
| 7,415,298 B2 | 8/2008 | Casciani et al. |
| 7,423,526 B2 | 9/2008 | Despotis |
| 2001/0020122 A1 | 9/2001 | Steuer et al. |
| 2003/0060693 A1 | 3/2003 | Monfre et al. |
| 2003/0088162 A1 * | 5/2003 | Yamamoto et al. ........... 600/310 |
| 2003/0220548 A1 | 11/2003 | Schmitt |
| 2004/0127777 A1 | 7/2004 | Ruchti et al. |
| 2004/0147034 A1 | 7/2004 | Gore et al. |
| 2004/0230106 A1 * | 11/2004 | Schmitt et al. ............... 600/310 |
| 2005/0113656 A1 | 5/2005 | Chance |
| 2005/0209516 A1 | 9/2005 | Fraden |
| 2005/0222502 A1 | 10/2005 | Cooper |
| 2005/0277818 A1 | 12/2005 | Myers |
| 2005/0277819 A1 | 12/2005 | Kiani et al. |
| 2006/0020179 A1 | 1/2006 | Anderson et al. |
| 2006/0020181 A1 | 1/2006 | Schmitt |
| 2006/0063995 A1 | 3/2006 | Yodh et al. |
| 2006/0084864 A1 | 4/2006 | Schmitt et al. |
| 2006/0167350 A1 | 7/2006 | Monfre et al. |
| 2006/0189859 A1 | 8/2006 | Kiani et al. |
| 2006/0189861 A1 | 8/2006 | Chen et al. |
| 2006/0195026 A1 | 8/2006 | Casciani et al. |
| 2006/0195027 A1 | 8/2006 | Casciani et al. |
| 2006/0200018 A1 | 9/2006 | Al-Ali |
| 2006/0211929 A1 | 9/2006 | Casciani et al. |
| 2006/0253016 A1 | 11/2006 | Baker, Jr. et al. |
| 2006/0264726 A1 | 11/2006 | Mannheimer et al. |
| 2006/0264727 A1 | 11/2006 | Mannheimer et al. |
| 2006/0276696 A1 | 12/2006 | Schurman |
| 2006/0281984 A1 | 12/2006 | Mannheimer et al. |
| 2007/0100218 A1 | 5/2007 | Sweitzer et al. |
| 2007/0100219 A1 | 5/2007 | Sweitzer et al. |
| 2007/0106137 A1 | 5/2007 | Baker, Jr. et al. |
| 2007/0118027 A1 | 5/2007 | Baker, Jr. et al. |
| 2007/0129614 A1 | 6/2007 | Schmitt et al. |
| 2007/0129622 A1 | 6/2007 | Bourget et al. |
| 2007/0135694 A1 | 6/2007 | Sato et al. |
| 2008/0033267 A1 | 2/2008 | Al-Ali |
| 2008/0139908 A1 | 6/2008 | Kurth |
| 2008/0188727 A1 | 8/2008 | Benaron et al. |
| 2008/0198361 A1 | 8/2008 | Kaushal et al. |

FOREIGN PATENT DOCUMENTS

| | | |
|---|---|---|
| DE | 19855521 A1 | 6/2000 |
| EP | 1135184 A1 | 6/2000 |
| EP | 1184663 A2 | 3/2002 |
| FR | 2710517 | 4/1995 |
| JP | 4-40940 | 2/1992 |
| JP | 5-329163 | 12/1993 |
| JP | 11-244266 | 9/1999 |
| JP | 2004 081427 A | 3/2004 |
| JP | 3635331 | 1/2005 |
| JP | 25095465 | 4/2005 |
| JP | 3797454 | 4/2006 |
| JP | 26201114 | 8/2006 |
| JP | 262797125 | 11/2006 |
| JP | 26326153 | 12/2006 |
| WO | WO 93/13706 A2 | 7/1993 |
| WO | WO 95/19562 A | 7/1995 |

| WO | WO 98/34097 | 8/1998 |
| WO | WO 00/32262 A1 | 6/2000 |
| WO | WO 00/71025 A1 | 11/2000 |
| WO | WO 01/16577 A1 | 3/2001 |
| WO | WO 03/010510 A | 2/2003 |
| WO | WO 2005/041765 A | 5/2005 |
| WO | WO2006097910 | 9/2006 |
| WO | WO2006124455 | 11/2006 |
| WO | WO2007048039 | 4/2007 |
| WO | WO2008020845 | 2/2008 |

OTHER PUBLICATIONS

"Study of Near Infrared Imaging of a Model of Brain Edema," Lee J. Jrohnson', Nitish Thakor' and Daniel Hanky'; 18th Annual International Conference of the IEEE Engineering in Medicine and Biology Society, Amsterdam 1996.*

Wheeler, Owen H., "Near Infrared Spectra of Organic Compounds," Department of Chemistry, College of Agriculture and Mechanic Arts, University of Puerto Rico (Mar. 1929).

Pace, Nello, et al., "Studies on Body Composition: III. The body water and chemically combined nitrogen content in relation to fat content," Naval Medical Research Institute, Bethesda, Maryland (Jan. 11, 1945).

Mitchell, H. M., et al., The Chemical Composition of the Adult Human Body and Its bearing on the Biochemistry of Growth), Division of Animal Nutrition, Departments of Physiology and Animal Husbandry, University of Illinois, pp. 625-637 (Feb. 1945).

Schloerb, Paul R., et al., "The Measurement of Total Body Water in the Human Subject by Deuterium Oxide Dilution," *Surgical Research Laboratories of the Peter Bent Brigham Hospital, and the Department of Surgery and the Biophysical Laboratory of the Harvard Medical School*, pp. 1296-1310 (Mar. 20, 1950).

Forbes, R.M., et al., "The Composition of the Adult Human Body as Determined by Chemical Analysis," Division of Animal Nutrition, and the Department of Anatomy, University of Illinois, Jan. 19, 1953.

Buijs, K., et al., "Near-Infrared Studies of the Structure of Water. I. Pure Water," *The Journal of Chemical Physics*, vol. 39, No. 8, pp. 2035-2041 (Oct. 15, 1963).

Choppin, G.R., et al., "Near-Infrared Studies of the Structure of Water. II. Ionic Soluation," *The Journal of Chemical Physics*, vol. 39, No. 8, pp. 2042-2050 (Oct. 15, 1963).

Goldstein, R., et al., "The Near-Infrared Absorption of Liquid Water at Temperatures Between 27 and 209° C.," *J. Quant. Spectrosc. Radiat. Transfer.*, vol. 4, pp. 441-451 (1964).

Ben-Gera, I., et al., "Influence of Fat Concentration on the Absorption Spectrum of Milk in the Near-Infrared Region," *Israel J. Agric. Res.*, Vo. 18, No. 3, pp. 117-124 (Jul. 1968).

Houseman, R.A., et al., "The measurement of total body water in living pigs by deuterium oxide dilution and its relation to body composition," *Br. J. Nutr.*, vol. 30, pp. 149-156 (1973).

Krikorian, S. Edward, et al., "The identification and origin of N-H overtone and combination bands in the near-infrared spectra of simple primary and secondary amides," *Spectrochimica Acta*, vol. 29A, pp. 1233-1246 (1973).

Lesser, G.T., et al., "Body water compartments with human aging using fat-free mass as the reference standard," *Am J. Physiol Regul Integr Comp Physiol.*, vol. 236, pp. 215-220 (1979).

Sheng, Hwai-Ping, et al., "A review of body composition studies with emphasis on total body water and fat," *The American Journal of Clinical Nutrition*, vol. 32., pp. 630-647 (Mar. 1979).

Martens, H., et al., "Unscrambling Multivariate Data from Mixtures: I: Fat, water and protein determination in meat by near-infrared reflectance spectroscopy, II: soy protein and collagen determination in meat products from amino acid data," *Meat Res. Workers, Proc. European Meeting*, pp. 146-149 (1980).

Fomon, Samuel J., et al., "Body composition of reference children from birth to age 10 years," The American Journal of clinical Nutrition, vol. 35, pp. 1169-1175, (May 1982).

Lanza, Elaine, "Determination of Moisture, Protein, Fat, and Calories in Raw Pork and Beef by near Infrared Spectroscopy," *Journal of Food Science*, vol. 48, pp. 471-474 (1983).

Shields, R. G., Jr., et al., "Efficacy of Deuterium Oxide to Estimate Body Composition of Growing Swine"; *Journal of Animal Science*, vol. 57, No. 1, pp. 66-73, (1983).

Wolfgang, Arneth, "Multivariate Infrared and near-infrared Spectroscopy: rapid analysis of protein, fat and water in meat," *Food Res and Data Analysis, Proc from IUoST Symp*, Oslo, Norway, pp. 239-251 (1983).

Cohn, S.H., et al., "Assessment of cellular mass and lean body mass by noninvasive nuclear techniques," *J. Lab Clin Med.*, vol. 105, pp. 305-311 (1985).

Hannon, John P., et al., "Splenic red cell sequestration and blood volume measurements in conscious pigs," *Am J. Physiol.*, vol. 248, pp. R293-R301 (1985).

Potts, R.O., et al., "A Noninvasive, In Vivo Technique to Quantitatively measure Water Concentration of the Stratum Corneum Using Attenuated Total-Reflectance Infrared Spectroscopy," *Arch. Dermatol Res.*, vol. 277, pp. 489-495 (1985).

Cox, Patrick, et al., "Variations in Lipids in Different Layers of Porcine Epidermis," *J. Invest Dermatol.*, vol. 87, pp. 741-744 (1986).

Valdes, E. V., et al., "Determination of Crude Protein and Fat in Carcass and Breast Muscle Samples of Poultry by Near Infrared Reflectance Spectroscopy," *Poultry Science*, vol. 65, pp. 485-490 (1986).

Hedberg, Christopher L., et al., "The Time Course of Lipid Biosynthesis in Pig Epidermis," *J. Invest Dermatol.*, vol. 91, pp. 169-174 (1988).

Hedberg, Christopher L., et al., "The nonpolar Lipids of Pig Epidermis," *J. Invest Dermatol.*, vol. 90, pp. 225-229 (1988).

Trapp, Scott A., et al., "An improved spectrophotometric bromide assay for the estimation of extracellular water volume," *Clinica Chimica Acta.*, vol. 1081, pp. 207-212, (1989).

Bommannan, D., et al., "Examination of Stratum Corneum Barrier Function In Vivo by Infrared Spectroscopy," *J. Invest Dermatol*, vol. 95, pp. 403-408 (1990).

Hannon, John P., et al., "Normal pHysiological Values for Conscious Pigs Used in Biomedical Research," *Laboratory Animal Science*, vol. 40, No. 3, May 1990.

Mak, Vivien H.W., et al., "Oleic Acid Concentration and Effect in Human Stratum Corneum: Non-Invasive determination By Attenuated Total Reflectance Infrared Spectroscopy In Vivo," *Journal of Controlled Release*, vol. 12, pp. 67-75 (1990).

Edwardson, P. et al., "The Use of FT-IR for the Determination of Stratum Corneum Hydration in Vitro and in Vivo," *J. of Pharmaceutical & Biomed. Analysis*, vol. 9, Nos. 10-12, pp. 1089-109, 1991.

Drummer, C., et al., "Effects of an acute saline infusion on fluid and electrolyte metabolism in humans," *Am J. Physiol.*, vol. 262, pp. F744-F754 (1992).

Horber, F.F., et al., "Impact of hydration status on body composition as measured by dual energy X-ray absorptiometry in normal volunteers and patients on haemodialysis," *The British Journal of Radiology*, vol. 65, pp. 895-900 (1992).

Schmitt et al., *Proc. SPIE*, "Measurement of blood hematocrit by dual-wavelength near-IP photoplethysmography," 1641:150-161 (1992).

Diaz-Carrillo, E., et al., "Near infrared calibrations for goat's milk components; protein, total casein, $α_s$-, β- and κ-caseins, fat and lactose," *J. near Infrared Spectrosc.*, vol. 1, pp. 141-146 (1993).

Martin, K., "Direct Measurement of Moisture in Skin by NIR spectroscopy," *J. Soc. Cosmet. Chem.*, 44:249-261 (1993).

Richard, Stéphanie, et al., "Characterization of the Skin In Vivo by High Resolution Magnetic Resonance Imaging: Water Behavior and Age-Related Effects," *The Journal of Investigative Dermatology*, vol. 100, No. 5, pp. 705-709 (May 1993).

Thompson et al., "Can bioelectrical impedance be used to measure total body water in dialysis patients?", *Physiol. Meas.*, 14:455-461 (1993).

Bewig, Karen M., et al., "Discriminant Analysis of Vegetable Oils by Near-Infrared Reflectance Spectroscopy," *JAOCS*, vol. 71, No. 2, pp. 195-200 (Feb. 1994).

Kamishikiryo-Yamashita, Hiromi, et al, "Protein Content in Milk by Near-Infrared Spectroscopy," *Journal of Food Science*, vol. 59, No. 2, pp. 313-315 (1994).

Matcher, S. J., et al., "Absolute quantification of deoxyhaemoglobin concentration in tissue near infrared spectroscopy," *Phys. Med. Biol.*, vol. 39, pp. 1295-1312 (1994).

Simanonok, Karl E., et al., "A Comprehensive Guyton Model Analysis of Physiologic Responses to Preadapting the Blood Volume as a Countermeasure to Fluid Shifts," *J. Clin Pharmacol*, vol. 34, pp. 440-453 (1994).

Steven, Alasdair C., et al., "Protein composition of cornified cell envelopes of epidermal keratinocytes," *Journal of Cell Science*, vol. 107, pp. 693-700 (1994).

Takeo, T. et al., "Skin Hydration State Estimation Using a Fiber-Optic Refractometer," *Applied Optics*, vol. 33, No. 19, Jul. 1994, p. 4267-72.

Warren, Joan L., et al., "The burden and Outcomes Associates with Dehydration among US Elderly, 1991," *American Journal of Public Health*, vol. 84, No. 8, pp. 1265-1269 (Aug. 1994).

Åneman, Anders, et al., "Splanchnic and Renal Sympathetic Activity in Relation to Hemodynamics During Isoflurane Administration in Pigs," *Anesth Analg.*, vol. 80, pp. 135-142, (1995).

Kisch, Hille, et al., "Accuracy and reproducibility of the measurement of actively circulating blood volume with an integrated fiberoptic monitoring system," *Critical Care Medicine*, vol. 23, No. 5, pp. 885-893 (1995).

Isaksson, Tomas, et al., "Non-Destructive Determination of Fat, Moisture and Protein in Salmon Fillets by User of Near-Infrared Diffuse Spectroscopy," *J. Sci Food Agric.*, vol. 69, pp. 95-100 (1995).

Quiniou, N., et al., "Prediction of Tissular Body Composition from Protein and Lipid Deposition in Growing Pigs," *J. Anim. Sci.*, vol. 73, pp. 1567-1575, (1995).

Avis, N.J., et al.; "In vitro multifrequency electrical impedance measurements and modeling of the cervix in late pregnancy", *Physiological Measurement*, vol. 17, pp. A97-103, 1996.

Gniadecka, M., et al., "Assessment of dermal water by high-frequency ultrasound: comparative studies with nuclear magnetic resonance," *British Journal of Dermatology*, vol. 135, pp. 218-224, (1996).

Finn, Patrick J., et al., "Progressive celluarl dehydration and proteolysis in critically ill patients," The Lancet vol. 347, pp. 654-646 (Mar. 9, 1996).

Johnson et al., "Monitoring of Extracellular and Total Body Water during Hemodialysis Using Multifrequency Bio-Electrical Impedance Analysis," *Kidney and Blood Pressure Research*, 19:94-99 (1996).

Kotler, D.P., et al.; "Prediction of body cell mass, fat-free mass, and total body water with bioelectrical impedance analysis: effects of race, sex, and disease;" *Am J. Clin. Nutr.* 64(suppl):489S-97S (1996).

Kumar, Gitesh, et al., "Non-Invasive Optical Assessment of Tissue Hydration," *International conference on Biomedical Engineering*, Jun. 3-5, 1996, Hong Kong, pp. C2-5.

Schmitt et al., *Proc. SPIE*, "Optimum wavelengths for measurement of blood hemoglobin content and tissue hydration by NIR spectrophotometry," 2678:442-453 (1996).

De Fijter, W.M., et al., "Asessement of total body water ad lean body mass from anthropometry, Watson formula, creatinine kinetics, and body electrical impedance compared with antipyrine kinetics and peritoneal dialysis patients," *Nephrol Dial Transplant*, vol. 12, pp. 151-156 (1997).

Johansen, Lars Bo, et al., "Hemodilution, central blood volume, and renal responses after an isotonic saline infusion in humans," *Am J. Physiol.*, vol. 272, pp. R549-R556 (1997).

Visser, Marjolein, et al., "Density of fat-free body mass: relationship with race, age, and level of body fatness," *Am J. Physiol.*, vol. 272, pp. E781-E787, (1997).

Alanen, Esko, et al., "Measurement of dielectric properties of subcutaneous fat with open-ended coaxial sensors," *Phys. Med. Biol.*, vol. 43, pp. 475-485 (1998).

Alanen, Esko, et al., "Variational Formulation of Open-Ended Coaxial line in Contact with Layered Biological Medium," *IEEE Transactions on Biomedical Engineering*, vol. 45, No. 10, pp. 1241-1248 (Oct. 1998).

Bonadonna, Riccardo C., et al., "Role of Tissue-Specific Blood Flow and Tissue Recruitment in Insulin-Mediated Glucose Uptake of Human Skeletal Muscl," *Circulation*, vol. 98, pp. 234-241, (1998).

Bracco, David, et al., "Bedside determination of fluid accumulation after cardiac surgery using segmental bioelectrical impedance," *Crit Care Med*, vol. 26, No. 6, pp. 1065-1070 (1998).

Gniadecka, Monika, et al., "Water and Protein Structure in Photoaged and Chronically Aged Skin," *J. Invest Dermatol*, vol. 111, pp. 1129-1133 (1998).

Gniadecka, Monika, et al., "Structure of Water, Proteins, and Lipids in Intact Human Skin, Hair, and Nail," *J. Invest Dermatol*, vol. 110, pp. 393-398 (1998).

Gow, Kenneth W., et al., "Effect of crystalloid administration on oxygen extraction in endotoxemic pigs," *J. Appl. Physiol.*, vol. 85, No. 5, pp. 1667-1675 (1998).

Husby, P., et al., "Midazolam-fentanyl-isoflurance anaesthesia is suitable for haemodynamic and fluid balance studies in pigs," *Laboratory Animals*, vol. 32, pp. 316-323 (1998).

Mitchell, A. D., et al., "Composition Analysis of Pork Carcasses by Dual-Energy X-Ray Absorptiometry," *J. Anim. Sci.*, vol. 76, pp. 2104-2114 (1998).

Mahan, D. C., et al., "Essential and Nonessential Amino Acid Composition of Pigs from Birth to 145 Kilograms of Body Weight, and Comparison to Other Studies," *J. Anim. Sci.*, vol. 76, pp. 513-521, (1998).

Martin, Kathleen, "In Vivo Measurements of Water in Skin by Near-Infrared Reflectance," *Applied Spectroscopy*, vol. 52, No. 7, 1998, pp. 1001-1007.

Schou, Henning, et al., "Uncompensated Blood Los is not Tolerated During Acute Normovolemic Hemodilution in Anesthetized Pigs," *Anesth Analg.*, vol. 87, pp. 786-794 (1998).

Stranc, M.F., et al., "Assessment of tissue viability using near-infrared spectroscopy," *British Journal of Plastic Surgery*, vol. 51, pp. 210-217, (1998).

Thomas, B. J., et al., "Bioimpedance Spectrometry in the Determination of Body Water Compartments: Accuracy and Clinical Significance," *Appl. Radiat. Isot.*, vol. 49, No. 5/6, pp. 447-455, (1998).

Wilhelm, K.P., "Possible Pitfalls in Hydration Measurements," *Skin Bioengineering Techniques and Applications in Dermatology and Cosmetology*, vol. 26, pp. 223-234 (1998).

Vrhovski, Bernadette, et al., "Biochemistry of tropoelastin," *Eur. J. Biochem.*, vol. 258, pp. 1-18 (1998).

Alanen, Esko, et al., "Penetration of electromagnetic fields of an open-ended coaxial probe between 1 MHz and 1 GHz in dielectric skin measurements," *Phys. Med. Biol.*, vol. 44, pp. N169-N176 (1999).

Dickens, Brian, et al., "Estimation of Concentration and Bonding Environment of Water Dissolved in Common Solvents Using Near Infrared Absorptivity," *J. Res. Natl. Inst. Stand. Technol.*, vol. 104, No. 2, pp. 173-183 (Mar.-Apr. 1999).

Fornetti, Willa C., et al., "Reliability and validity of body composition measures in femal athletes," Journal of Applied Physiology, vol. 87, pp. 1114-1122, (1999).

Fusch, Christoph, et al., "Neonatal Body COmposition: Dual-Energy X-Ray Absorptiometry, Magnetic Resonance Imaging, and Three-Dimensional Chemical Shift Imaging *versus* Chemical Analysis in Piglets," *Pediatric Research*, vol. 46, No. 4, pp. 465-473 (1999).

Gudivaka, R., et al., "Single- and multifrequency models for bioelectrical impedance analysis of body water compartments," *J. Appl. Physiol.*, vol. 87, No. 3, pp. 1087-1096 (1999).

Jennings, Graham, et al., "The Use of infrared Spectrophotometry for Measuring Body Water Spaces," vol. 45, No. 7, pp. 1077-1081 (1999).

Kalantar-Zadeh, Kamyar, et al., "Near infra-red interactance for nutritional assessment of dialysis patients," *Nephrol Dial Transplant*, vol. 14, pp. 169-175 (1999).

Kayser-Jones, Jeanie, et al., "Factors Contributing to Dehydration in Nursing Homes: Inadequate Staffing and Lack of Professional Supervision," *J. Am Geriatr. Soc.*, vol. 47, pp. 1187-1194 (1999).

Lange, Neale R., et al., "The measurement of lung water," *Critical Care*, vol. 3, pp. R19-R24 (1999).

Marken Lichtenbelt, Wouter D. Van, et al., "Increased extracellular water compartment, relative to intracellular water compartment, after weight reduction," *Journal of Applied Physiology*, vol. 87, pp. 294-298 (1999).

Rennie, Michael J., "Perspectives—Testing out the truth about collagen," *Journal of Physiology*, vol. 521, p. 1 (1999).
Sowa et al., "Near-infrared spectroscopic assessment of tissue hydration following surgery", *Journal of Surgical Research*, 86:62-69 (1999).
Wagner, J.R., et al., "Analysis of Body Composition Changes of Swine During Growth and Development," *J. Anim. Sci.*, vol. 77, pp. 1442-1466 (1999).
Wang, Zimian, et al., "Hydration of fat-free body mass: new physiological modeling approach," *Am. J. Physiol.*, vol. 276, pp. E995-E1003 (1999).
Wang, Zimian, et al., "Hydration of fat-free body mass: review and critique of a classic body-composition constant," *Am J. Clin. Nutr.*, vol. 69, pp. 833-841 (1999).
Ward, L., et al., "Multiple frequency bioelectrical impedance analysis: a cross-validation study of the inductor circuit and Cole models," *Physiol. Meas.*, vol. 20, pp. 333-347 (1999).
Well, Jonathan CK, et al., "Four-component model of body composition in children: density and hydration of fat-free mass and comparison with simpler models," *Am J. Clin. Nutr.*, vol. 69, pp. 904-912 (1999).
Butte, Nancy F., et al., "Body Composition during the First 2 Years of Life; An Updated Reference," *Pediatric Research*, vol. 47, No. 5, pp. 578-585 (2000).
Feigenbaum, Matthew S., et al., "Contracted Plasma and Blood Volume in Chronic Heart Failure," *J Am Coll. Cardiol.*, vol. 35, No. 1, pp. 51-55 (Jan. 2000).
Kays, Sandra E., et al., "Predicting protein content by near infrared reflectance spectroscopy in diverse cereal food products," *J. Near Infrared Spectrosc.*, vol. 8, pp. 35-43 (2000).
Lucassen, G., et al., "Water Content and Water Profiles in Skin Measured by FTIR and Raman Spectroscopy," *Proc. SPIE*, vol. 4162, pp. 39-45 (2000).
Plank, L. D., et al., "Similarity of Changes in Body Composition in Intensive Care Patients following Severe Sepsis or Major Blunt Injury," *Annals New York Academy of Sciences*, pp. 592-602 (2000).
Ritz, P., et al., "Body Water Spaces and Cellular Hydration Using Healthy Aging," *Annals New York Academy of Sciences*, pp. 474-483 (2000).
Schoeller, Dale, "Bioelectrical Impedance Analysis—What does it measure?" *Annals New York Academy of Sciences*, pp. 159-162 (2000).
Starcher, Barry C., "Lung Elastin and Matrix," *Chest*, vol. 117, No. 5, pp. 229S-234S, May 2000 Supplplement.
Young, A.E.R., et al., "Behaviour of near-infrared light in the adult human head: implications of clinical near-infrared spectroscopy," *British Journal of Anaesthesia*, vol. 84, No. 1, pp. 38-42 (2000).
Zembrzuski, Cora, "Nutrition and Hydration," Best Practices in Nursing Care to Older Adults, The Hartford Institute for Geriatric Nursing, vol. 2, No. 2, Sep. 2000, 2 pages.
Attas, Michael, et al., "Visualization of cutaneous hemoglobin oxygenation and skin hydration using near-infrared spectroscopic imaging," *Skin Research and Technology*, vol. 7, pp. 238-245, (2001).
Bray, George A., et al., "Evaluation of body fat in fatter and leaner 10-y-old African American and white children: the Baton Rouge Children's Study," *Am J. Clin Nutr*, vol. 73, pp. 687-702 (2001).
Campbell, Wayne W., et al., "The Recommended Dietary Allowance for Protein May Not Be Adequate for Older People to Maintain Skeletal Muscle," *Journal of Gerontology*, vol. 56A, No. 6, pp. M373-M380 (2001).
Divert, Victor E., "Body Thermal State Influence on Local Skin Thermosensitivity," *International Journal of Circumpolar Health*, vol. 60, pp. 305-311 (2001).
Du, Y., et al., "Optical properties of porcine skin dermis between 900 nm and 1500 nm," *Phys. Med. Biol.*, vol. 46, pp. 167-181 (2001).
Endo, Yutaka, et al., "Water drinking causes a biphasic change in blood composition in humans," *Pflügers Arch—Eur J. Physiol*, vol. 442, pp. 362-368 (2001).
Garaulet, Marta, et al., "Site-specific differences in the fatty acid composition of abdominal adipose tissue in an obese population from a Mediterranean area: relation with dietary fatty acids, plasma lipid profile, serum insulin, and central obesity," *Am J. Clin. Nutr.*, vol. 74, pp. 585-591 (2001).

Haga, Henning A., et al., "Electroencephalographic and cardiovascular indicators of nociception during isoflurane anaesthesia in pigs," *Veterinary Anaesthesia and Analgesia*, vol. 28, pp. 126-131 (2001).
Kalantar-Zadeh, Kamyar, et al., "Near infra-red interactactance for Longitudinal Assessment of Nutrition in Dialysis Patients," *Journal of Renal Nutrition*, vol. 11, No. 1, pp. 23-31 (Jan. 2001).
Kamba, Masayuki, et al., "Proton magnetic resonance spectroscopy for assessment of human body composition," *Am J. Clin. Nutr.*, vol. 73, pp. 172-176 (2001).
Lever, M., et al., "Some ways of looking at compensatory kosmotropes and different water environments," *Comparative Biochemistry and Physiolog.*, vol. 130, Part A, pp. 471-486, (2001).
Mingrone, G., et al., "Unreliable use of standard muscle hydration value in obesity," *Am. J. Physiol Endocrinal Metab.*, vol. 280, pp. E365-371, (2001).
Šašic, Slobodan, et al., "Short-Wave Near-Infrared Spectroscopy of Biological Fluids. 1. Quantitative Analysis of Fat, Protein, and Lactose in Raw Milk by Partial Least-Squares Regression and Band Assignment," *Anal. Chem.*, vol. 73, pp. 64-71 (2001).
Schnickel, A.P., et al., "Evaluation of alternative measures of pork carcass composition," *J. Anim. Sci.*, vol. 79, pp. 1093-1119, (2001).
Sowa et al., "Near infrared spectroscopic assessment of hemodynamic changes in the early post-burn period," *Burns*, 27(3):241-9 (2001).
Troy, Tamara L., et al., "Optical properties of human skin in the near infrared wavelenth range of 1000 to 2200nm," *Journal of Biomedical Optics*, vol. 6, No. 2, pp. 167-176 (Apr. 2001).
Tsukahara, K., et al., "Dermal fluid translocation is an important determinant of the diurnal variation in human skin thickness," *British Journal of Dermatology*, vol. 145, pp. 590-596 (2001).
Vescovi, Jason D., et al., "Evaluation of the BOD POD for estimating percentage body fat in a heterogeneous group of adult humans," *Eur. J. Appl. Physiol.*, vol. 85, pp. 326-332 (2001).
Wang, Zimian, et al., "Magnitude and variation of ratio of total body potassium to fat-free mass: a cellular level modeling study," *Am J. Physiol. Endocrinal. Metab*, vol. 281, pp. E1-E7, (2001).
Watson, Walter, "Hydration of fat-free body mass: new physiological modeling approach," *Am J. Physiol. Endocrinol. Metab.*, Letters to the Editor, vol. 278, pp. E752-E753 (2001).
Attas, E. Michael, et al., "Near-IR Spectroscopic Imaging for Skin Hydration: The Long and the Short of It," *Biopolymers*, vol. 67, No. 2, pp. 96-106 (2002).
Attas, M. et al., "Long-Wavelength Near-Infrared Spectroscopic Imaging for In-Vivo Skin Hydration Measurements," *Vibrational spectroscopy* (Feb. 28, 2002), vol. 28, No. 1, p. 37-43.
Blank, T.B., et al., "Clinical Results from a Non-Invasive Blood Glucose Monitor," *Photonics West 2000 Meeting*, San Jose, California, Jan. 19-25, 2002 (25 pages).
Chamney, Paul W., et al., "A new technique for establishing dry weight in hemodialysis patients via whole body bioimpedance," *Kidney International*, vol. 61, pp. 2250-2258 (2002).
Drobin, Dan, et al., "Kinetics of Isotonic and Hypertonic Plasma Volume Expanders," *Anesthesiology*, vol. 96, No. 6, pp. 1371-1380 (Jun. 2002).
Endo, Yutaka, et al., "Changes in Blood Pressure and Muscle Sympathetic Nerve Activity during Water Drinking in Humans," *Japanese Journal of Physiology*, vol. 52, pp. 421-427 (2002).
Haga, Henning A., et al., "Motor responses to stimulation during isoflurane anaesthesia in pigs," *Veterinary Anaesthesia and Analgesia*, vol. 29, pp. 69-75 (2002).
Klaus, Stephan, et al., "Assessment of fluid balance by measurement of skin tissue thickness during clinical anaesthesia," *Clin. Physiol. & Func. Im.*, vol. 22, pp. 197-201 (2002).
Meglinski, Igor V., et al., "Quantitative assessment of skin layers absorption and skin reflectance spectra simulation in the visible and near-infrared spectral regions," *Physiol. Meas.*, vol. 23, pp. 741-753, (2002).
Perez-de-Sá, Valéria, et al., "Mild Hypothermia Has Minimal Effects on the Tolerance to Severe Progressive Normovolemic Anemia in Swine," *Anesthesiology*, Vo. 97, pp. 1189-1197 (2002).
Ponec, Maria, et al., "Characterization of Reconstructed Skin Models," *Skin Pharmacol Appl Skin Physiol.*, vol. 15, Supplement 1, pp. 4-17, (2002).

Querleux, B., et al., "Anatomy and physiology of subcutaneous adipose tissue by in vivo magnetic resonance imaging and spectroscopy: Relationships with sex and presence of cellulite," *Skin Research and Technology*, vol. 8, pp. 118-124 (2002).

Van Brommel, Jasper, et al., "Intestinal and Cerebral Oxygenation during Severe Isovolemic Hemodilution and Subsequent Hyperoxic Ventilation in a Pig Model," *Anesthesiology*, vol. 97, No. 3, pp. 660-670 (Sep. 2002).

Wong, William W., et al., "Evaluating body fat in girls and female adolescents: advantages and disadvantages of dual-energy X-ray absorptiometry," *Am. J. Clin Nutr*., vol. 76, pp. 384-389 (2002).

Baković, Darija, et al., "Spleen volume and blood flow response to repeated breath-hold apneas," *J. Appl. Physiol.*, vol. 95, pp. 1460-1466 (2003).

Bartok, Cynthia, et al., "Measurement of nutritional status in simulated microgravity by bioelectrical impedance spectroscopy," *J. Appl. Physiol.*, vol. 95, pp. 225-232 (2003).

Bouwstra, Joke A., et al., "Water Distribution and Related Morphology in Human Stratum Corneum at Different Hydration Levels," *J. Invest Dermatol*, vol. 150, pp. 750-758 (2003).

Butte, Nancy F., et al., "Composition of gestational weight pain impacts maternal fat retention and infant birth weight," *Am J. Obstet Gynecol*, vol. 189, pp. 1423-1432 (2003).

Cloonan, Clifford C., "Don't Just Do Something, Stand There!: To Teach of not to Teach, That is the Question—Intravenous Fluid Resuscitation Training for Combat Lifesavers," *The Journal of Trauma, Injury, Infection, and Critical Care*, vol. 54, No. 5, pp. S20-S25 (May Supplement 2003).

Cook, Lynda S., "IV Vluid Resuscitation," *Journal of Infustion Nursing*, vol. 26, No. 5, pp. 296-303 (Sep./Oct. 2003).

Dey, D.K., et al., "Body composition estimated by bioelectric impedance in the Swedish elderly. Development of population-based prediction equation and reference values of fat-free mass and body fat for 70- and 75-y olds," *European Journal of Clinical Nutrition*, vol. 57, pp. 909-916 (2003).

Farstad, M., et al., "Fluid extravasation during cardiopulmonary bypass in piglets—effects of hypothermia and different cooling protocols," *Acta Anaesthesiol. Scand.*, vol. 47, pp. 397-406 (2003).

Grandjean et al., "Hydration: issues for the $21^{st}$ century", *Nutrition Reviews*, 61(8):261-271 (2003).

Heise, H.M., et al., "Reflectance spectroscopy can quantify cutaneous haemoglobin oxygenation by oxygen uptake from the atmosphere after epidermal barrier distruption," *Skin Research and Technology*, vol. 9, pp. 295-298 (2003).

Kasemsumran, Sumaporn, et al., "Simultaneous determination of human serum albumin, γ-globulin, and glucose in a phosphate buffer solution by near-infrared spectroscopy with moving window partial least-square regression," *Analyst*, vol. 128, pp. 1471-1477 (2003).

Kemming, G.I., et al., "Hyperoxic ventilation at the critical haematocrit," *Resuscitation*, vol. 56, pp. 289-297 (2003).

Kurita, T., et al., "Comparison of isoflurane and propofol-fentanyl anaesthesia in a swine model of asphyxia," *British Journal of Anaesthesia*, vol. 91, No. 6, pp. 871-877 (2003).

Laaksonen, DE, et al., "Changes in abdominal subcutaneous fat water content with rapid weight loss and long-term weight maintenance in abdominally obese men and women," *International Journal of Obesity*, vol. 27, pp. 677-683 (2003).

Mao, Jinshu, et al., "Study of Novel Chitosan-gelatin artificial skin in vitro," *J. Miomed Mater Res.*, vol. 64, Part A, pp. 301-308 (2003).

Mauran, P., et al., "Renal and hormonal responses to isotonic saline infusion after 3 days' dead-down tilt vs. supine and seated positions," *Acta Physiol. Scand.*, vol. 177, pp. 167-176, (2003).

McHugh, Gerard, "Letter—Passive leg elevation and head-down tilt: effects and duration of changes," *Critical Care*, vol. 7, No. 3, p. 246 (Jun. 2003).

Meglinski, I.V., et al., "Computer simulation of the skin reflectance spectra," *Computer Methods and Programs in Biomedicine*, vol. 70, pp. 179-186, (2003).

Mendelsohn, Richard, et al., "Infrared microspectroscopic imaging maps the spatial distribution of exogenous molecules in skin," *Journal of Biomedical Optics*, vol. 8, No. 2, pp. 185-190 (Apr. 2003).

Mentes, Janet C., et al., "Reducing Hydration=-Linked events in Nursing Home Residents," *Clinical Nursing Research*, vol. 12, No. 3, pp. 210-225 (Aug. 2003).

Merritt, Sean, et al., "Coregistration of diffuse optical spectroscopy and magnetic resonance imaging in a rat tumor model," *Applied Optics*, vol. 42, No. 16, pp. 2951-2959 (Jun. 2003).

Parker, Lisa, et al., "Validity of Six Field and Laboratory Methods for Measurement of Body Composition in Boys," *Obesity Research*, vol. 11, No. 7, pp. 852-858 (Jul. 2003).

Petäjä L., et al., "Dielectric constant of skin and subcutaneous fat to assess fluid changes after cardiac surgery", *Physiological Measurement*, 24: 3383-390, 2003.

Rhodes, Andrew, et al., "Book Report—Haemodynamic monitoring in critically ill patients," *Critical Care*, vol. 8, p. 203 (2004).

Richardson, Andrew D., et al., "Multivariate analyses of visible/near infrared (VIS/NIR) absorbance spectra reveal underlying spectral differences among dried, ground confier needle samples from different growth environments," *New Phytologist*, vol. 161, pp. 291-301 (2003).

Ritz, Patrick, "Chronic Cellular Dehydration in the Aged Patient," Journal of Gerontology, vol. 56A, No. 6, pp. M349-M352 (2001).

Robinson, Martin P., et al., "A novel method of studying total body water content using a resonant cavity: experiments and numerical simulation," Phys. Med. Biol., vol. 48, pp. 113-125, (2003).

Sergi, Giuseppe, et al., "Changes in Fluid Compartments and Body Composition in Obese Women after Weight Loss Induced by Gastric Banding," *Ann. Nutr Metab.*, vol. 47., pp. 152-157 (2003).

Wang, Zimian, et al., "Magnitude and variation of fat-free mass density: a cellular level body composition modeling study," *Am J. Physiol. Endocrinal. Metab*, vol. 284, pp. E267-E273 (2003).

Windberger, U, et al., "Whole blood viscosity, plasma viscocity and erythrocyte aggregation in nine mammalian species; reference values and comparison of data," *Exp., Physiol.*, vol. 88, No. 3, pp. 431-440 (2003).

Wolf, Martin, et al., "Absolute Frequency-Domain pulse Oximetry of the Brain: Methodology and Measurements," *Oxygen Transport to Tissue XXIV*, Chapter 7, Dunn and Swartz, Kluwer Academic/Plenum Publishers, pp. 61-73 (2003).

Ackland, G.L., et al., "Assessment of preoperative fluid depletion using bioimpedance analysis," *British Journal of Anaesthesia*, vol. 92, No. 1, pp. 134-136 (2004).

Arimoto et al., "Non-contace skin moisture measurement based on near-infrared spectroscopy", *Applied Spectroscopy*, 58(12):1439-1445 (2004).

Davidhizr, R., et al., "A review of the literature on how important water is to the world's elderly population," *International Nursing Review*, vol. 51, pp. 159-166 (2004).

Dullenkopf, A., et al., "Non-invasive monitoring of haemoglobin concentration in paediatric surgical patients using near-infrared spectroscopy," *Anaesthesia*, vol. 59, pp. 453-458 (2004).

Finlay, Jarod C., et al., "Hemoglobin oxygen saturations in phantoms and in vivo from measurements of steady-state diffuse reflectance at a single, short source-detector separation," *Medical Physics*, vol. 31, No. 7, pp. 1949-1959 (Jul. 2004).

Hendriks, F.M., et al., "Influence of hydration and experimental length scale on the mechanical response o human skin in vivo, using optical coherence tomography," *Skin Research and Technology*, vol. 10, pp. 231-241 (2004).

Hieda, I., et al., "Basic characteristics of the radio imaging method for biomedical application," *Medical Engineering & Physics*, vol. 26, pp. 431-437 (2004).

Ikizler, T. Alp, et al., "Urea space and total body water measurements by stable isotopes in patients with acute renal failure," *Kidney International*, vol. 65, pp. 725-732 (2004).

Isenring, E., et al., "Evaluation of foot-to-foot bioelectrical impedance analysis for the prediction of total body water in oncology outpatients receiving radiotherapy," *European Journal of Clinical Nutrition*, vol. 58, pp. 46-51 (2004).

Jacobi, Ute, et al., "In vivo determination of skin surface topography using an optical 3D device," *Skin Research and Technology*, vol. 10, pp. 207-214 (2004).

Kao, Bunsho, et al., "Evaluation of Cryogen Spray Cooling Exposure on In Vitro Model Human Skin," *Lasers in Surgery and Medicine*, vol. 34, pp. 146-154 (2004).

Kyle, Urusula G., et al., Bioelectrical impedance anslysis—part II: utilization in clinical practice, *Clinical Nutrition*, vol. 23, pp. 1430-1453 (2004).

Lof, Marie, et al., "Hydration of fat-free mass in healthy women with special reference to the effect of pregnancy," *Am J. Clin. Nutr.*, vol. 80, pp. 960-965 (2004).

Lowrie, Edmund G., "Urea space and body water," *Kidney Intl.*, vol. 66, No. 2, p. 868, Aug. 2004.

Mirrashed, F., et al., "Pilot study of dermal and subcutaneous fat structures by MRI in individuals who differ in gender, BMI, and cellulite grading," *Skin Research and Technology*, vol. 10, pp. 161-168 (2004).

Mirrashed, Fakhereh, et al., "In vivo morphological characterization of skin by MRI micro-imaging methods," *Skin Research and Technology*, vol. 10, pp. 149-160, (2004).

Notingher, Ioan, et al., "Mid-infrared in vivo depth-profiling of topical chemicals on skin," *Skin Research and Technology*, vol. 10, pp. 116-121, (2004).

Nouveau-Richard, S., et al., "In vivo epidermal thick ness measurement: ultrasound vs. confocal imaging," *Skin Research and Technology*, vol. 10, pp. 136-140, (2004).

Nuutinen, J., et al., "Validation of a new dielectric device to assess changes of tissue water in skin and subcutaneous fat," *Physiol. Meas.*, vol. 25, pp. 447-454, (2004).

St-Onge, Marie-Pierre, et al., "Dual-energy X-ray absorptiometry lean soft tissue hydration: independent contributions of intra-and extracellular water," *Am J. Physiol. Endrocrinol Metab*, vol. 287, pp. E842-E847, Jul. 6, 2004.

Schou, A. J., et al., "Methodological aspects of high-freqeuncy ultrasound of skin in children," *Skin Research and Technology*, vol. 10, pp. 200-206, (2004).

Stone, Darren A., et al., "Total body water measurements using resonant cavity perturbation techniques," *Phys. Med. Biol.*, vol. 49, pp. 1773-1788, (2004).

Takiwaki, Hirotsugu, et al., "Analysis of the absorbance spectra of skin lesions as a helpful tool for detection of major pathophysiological changes," *Skin Research and Technology*, vol. 10, pp. 130-135 (2004).

Van Kemenade, Patricia M., et al., "Do somotic forces play a role in the uptake of water by human skin?", *Skin Research and Technology*, vol. 10, pp. 109-112 (2004).

Wang, Zimian, et al., "Body cell mass: model development and validation at the cellular level of body composition," *Am J. Physiol. Endrocrinol. Metab.*, vol. 286, pp. E123-E128 (2004).

Arimoto, Hidenobu, et al., "Depth profile of diffuse reflectance near-infrared spectroscopy for measurement of water content in skin," *Skin Research and Technology*, vol. 11, pp. 27-35 (2005).

Burmeister, J.J., et al., "Spectroscopic considerations for noninvasive blood glucose measurements with near infrared spectroscopy", *LEOS Newsletter*, vol. 12, No. 2, 1998, http://www.ieee.org/organizations/pubs/newsletters/leos/apr98/infrared.htm (last assessed, Nov. 30, 2005).

Haroun, D., et al., "Composition of the fat-free mass in obese and nonobese children: matched case—control analyses," *International of Obesity*, vol. 29, pp. 29-36 (2005).

Ivorra, Antoni, et al., "Bioimpedance dispersion width as a parameter to monitor living tissues," *Physiol. Meas.*, vol. 26, pp. S165-S173 (2005).

Fischman, Josh, Remote ICU Monitoring, *U.S. News & World Report*, pp. 45-61 (Aug. 1, 2005).

Sarkar, Shubho R., et al., "Assessment of Body Composition in Long-Term Hemodialysis Patients: Rationale and Methodology," *Journal of Renal Nutrition*, vol. 15, No. 1, pp. 152-158 (Jan. 2005).

Youcef-Toumi K., et al., "Noninvasive blood glucose analysis using near infrared absorption spectroscopy", MIT Home Automation and Healthcare Consortium, Progress Report No. 2-5, http://darbelofflab.mit.edu/ProgressReports/HomeAutomation/Report2-5/Chapter04.pdf (last accessed, Nov. 30, 2005).

Garcia-Olmo, J., et al., "Advantages and disadvantages of multiple linear regression and partial least squares regression equations for the prediciton of fatty acids," pp. 253-258 (undated).

Wang, Zimian, et al., "Cellular-Level Body Composition Model—A New Approach to Studying Fat-free Mass Hydration," *Annals New York Academy of Science*, pp. 306-311 (undated).

Adeloye, Adelola, et al., "Thickness of the Normal Skull in the American Blacks and Whites," A. J. Phys. Anthrop., 43: 23-30.

Hayman, L. Anne, et al., "Clinical and Imaging Anatomy of the Scalp," 2003 Journal of Computer Assisted Tomography 27(3):454-459.

Kampfl, A., et al., "Near Infrared Spectroscopy (NIRS) in Patients with Severe Brain Injury and Elevated Intracranial Pressure," Acta Neurochir (1997) [Suppl] 70:112-114.

Thiagarajah, Jay R., et al., "Noninvasive Early Detection of Brain Edema in Mice by Near-Infrared Light Scattering," 2005 Journal of Neuroscience Research 80:293-299.

U.S. Appl. No. 11/528,154, filed Sep. 27, 2006, Debreczeny et al.

U.S. Appl. No. 11/528,218, filed Sep. 27, 2006, Campbell et al.

J. H. Ali, et al.; "Near Infrared Spectroscopy and Imaging to Prove differences in Water content in normal and Cancer Human Prostate Tissues", *Technology in Cancer Research & Treatment*, vol. 3, No. 5, Oct. 2004; pp. 491-497.

* cited by examiner

SYSTEM AND METHOD FOR DETECTION OF BRAIN EDEMA USING SPECTROPHOTOMETRY

BACKGROUND OF THE INVENTION

1. Field of the Invention

The present invention relates generally to a method and system for detecting swelling occurring as a result of increased water content in and around the brain. Specifically, embodiments of the present invention relate to detecting water content and measuring changes in microcirculation in and around brain tissue to facilitate diagnoses and monitoring of brain edema.

2. Description of the Related Art

This section is intended to introduce the reader to various aspects of art that may be related to various aspects of the present invention, which are described and/or claimed below. This discussion is believed to be helpful in providing the reader with background information to facilitate a better understanding of the various aspects of the present invention. Accordingly, it should be understood that these statements are to be read in this light, and not as admissions of prior art.

Edema may be generally defined as swelling caused by excess fluid in body tissues. Brain edema may be specifically described as swelling in the brain due to an increase in its water content, or as an accumulation of excessive fluid in the substance of the brain. Brain edema may also be referred to as cerebral edema, brain swelling, wet brain, swelling of the brain, and so forth.

The brain is especially susceptible to injury from edema because it is located within a confined space (i.e., the skull) and, thus, cannot expand. The human skull is essentially a rigid fluid filled container. Principle constituents within the skull include brain tissue, blood, and cerebral-spinal fluid (CSF). Because the skull is essentially rigid and has a constant volume, if there is an increase in the volume of the contents of the skull (e.g., as a result of brain edema), the pressure inside the skull (i.e., intracranial pressure) will rise unless some fluid is able to escape. For example, if the brain tissue experiences swelling, a certain amount of blood or CSF must escape the skull cavity to prevent a rapid increase in pressure. During such swelling, pressure inside the skull may rise above the normal range. Further, if swelling continues until little or no fluid remains, any further swelling will cause a rapid increase in intracranial pressure (ICP). A sufficient rise in ICP may cause compromised blood supply to the brain and herniation of the cerebral content through an opening in the skull. Thus, untreated brain edema may lead to neurological degeneration, loss of consciousness, and death.

Causes of brain edema include head trauma, vascular insults, abnormal metabolic conditions, infections, space-occupying lesions, and toxicity. The mechanisms of brain edema are cytotoxic and vasogenic. Cytotoxic edema is generally caused by neuronal damage that leads to increased sodium and water in the brain cells. Vasogenic edema is generally a result of vascular trauma causing leakage of protein from blood into the extracellular compartment. Water generally moves into the extracellular compartment as a result of increased osmotic pressure.

Brain edema may be suspected in a patient if the patient presents with a headache, vomiting, altered consciousness, and/or sensorium. Additionally, upon examination of the patient, further indicators may be observed. For example, the patient may be determined to have papilloedema (i.e., swelling of the optic disc) based on fundoscopy (i.e., examination of the interior of the eye), unilateral or bilateral motor posturing, changing breathing patterns, circulatory hemodynamics, and so forth. Diagnosis may be confirmed by imaging techniques such as a computed tomography (CT) scan. Once the diagnosis is confirmed, the ICP may be monitored (e.g., via placement of catheters in the cranial cavity).

Traditional techniques for monitoring and measuring ICP generally involve the use of invasive devices. For example, commonly used devices include hollow screw and bolt devices. These typically include metallic cylindrical instruments which are inserted into the patient such that an instrument tip protrudes into the subarachnoid space to facilitate pressure measurement. The subarachnoid space may be defined as the compartment within the spinal column that contains the CSF. Another commonly used invasive device for ICP monitoring is an intraventricular catheter. The intraventricular catheter is typically placed inside ventricles (i.e., fluid filled cavities) of the brain to facilitate pressure monitoring. Insertion of such invasive devices (e.g., hollow screws and catheters) to facilitate ICP monitoring can be undesirable.

Some existing techniques for monitoring ICP are non-invasive. For example, some existing methods involve emitting ultrasound into the patient's brain to facilitate detection of an elevated ICP. Such ultrasound emissions typically reach the brain through natural windows in the skull. For example, ultrasound emissions may be introduced to a patient's brain via an eye socket. However, these ultrasound emissions may be undesirable depending on how long the eye must be esonified. Further, sensor placement for such methods can be difficult, resulting in inaccuracies.

BRIEF DESCRIPTION OF THE DRAWINGS

Advantages of the invention may become apparent upon reading the following detailed description and upon reference to the drawings in which.

DETAILED DESCRIPTION OF SPECIFIC EMBODIMENTS

One or more specific embodiments of the present invention will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

Embodiments of the present invention relate generally to detecting brain edema by estimating water content in and around brain tissue using photospectrometry. Specifically, present embodiments may include procedures and devices that facilitate diagnosis and monitoring of brain edema. For example, one embodiment may be utilized to detect brain edema with diffusely reflected near infrared spectroscopy (NIRS) that facilitates calculation of local brain tissue water content and/or measurement of changes in microcirculation in and around the brain. Further, present embodiments may include both invasive and non-invasive applications.

Figure 1:
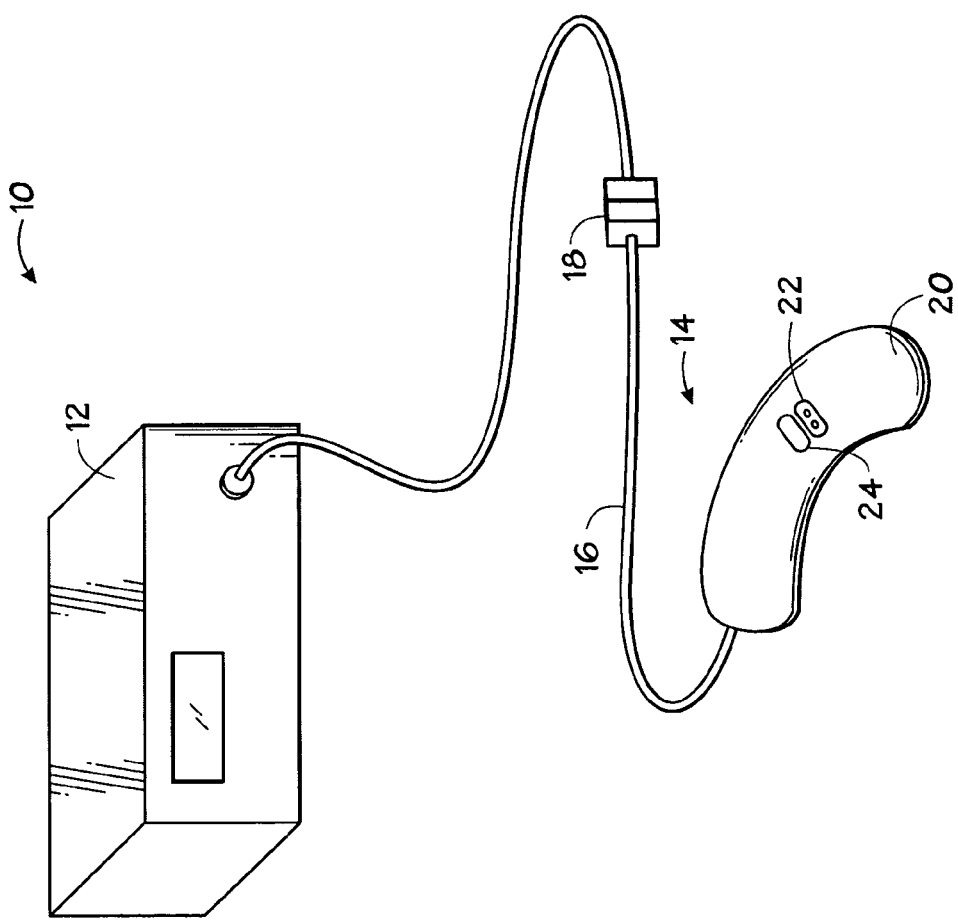
FIG. 1 is a perspective view of a tissue hydration monitoring system in accordance with an exemplary embodiment of the present invention.

FIG. 1 is a perspective view of a brain tissue hydration measurement system 10 in accordance with an exemplary embodiment of the present invention. The system 10 includes a hydration monitor 12 (e.g., computer) that communicatively couples to a sensor 14. The sensor 14 includes a sensor cable 16, a connector plug 18, and a body 20 configured to attach to a patient. The sensor 14 may couple directly to a patient's brain tissue, or the sensor 14 may couple to an area proximate the patient's brain tissue. For example, in one embodiment, the sensor 14 may be non-invasive and the body 20 of the sensor 14 may be configured to externally couple to a patient's forehead (e.g., via an adhesive material). In another embodiment, the sensor 14 may be invasive and have a body 20 that is configured to facilitate physical contact with the patient's brain tissue. The sensor cable 16 and connector plug 18 may enable electronic communication from the sensor 14 to the monitor 12, and facilitate coupling and/or decoupling of the sensor 14 from the monitor 12. In some embodiments, the sensor 14 couples directly to the monitor 12 via the sensor cable 16. Further, it should be noted that in some embodiments, the sensor 14 communicates with the monitor 12 wirelessly (e.g., via radio waves) and does not include the cable 16 or the connector plug 18.

The brain tissue hydration measurement system 10 may be utilized to observe the water content of tissue or tissuular hydration in and around the brain to facilitate detection and/or monitoring of brain edema. This may be achieved spectroscopically by the system 10 because the absorbance of certain light wavelengths by brain tissue may correlate to water content. For example, a level of tissular hydration may be estimated by emitting signals or waves into the patient's tissue and detecting the waves after dispersion and/or reflection by the tissue. For example, one embodiment of system 10 may emit light from a light source 22 (e.g., two or more light emitting diodes (LEDs)) into the brain tissue and then detect the transmitted light with a light detector 24 (e.g., a photodiode or photo-detector) after the light has passed through the brain tissue. The amount of transmitted light that passes through the brain tissue may vary in accordance with varying amounts of constituents (e.g., water) present in the tissue and the corresponding variance of light absorption characteristics. Accordingly, the amount of detected light may be correlated to an amount of tissular hydration, which may be used to monitor or detect brain edema. Brain tissue is composed of approximately 70% water whereas brain interstitial fluid is composed of more than 90% water. Accordingly, an increase in the ratio of interstitial fluid to brain tissue, such as may be caused by edema, can therefore be expected to lead to an increase in net water content (or hydration).

Embodiments of the present invention utilize reflectance NIRS to measure a fraction of water (i.e., a water fraction) present in and/or around brain tissue. The water fraction may be defined spectroscopically as the ratio of the absorbance of water and the sum of the absorbances of water and other constituents of the tissue. An increase or decrease in the water content of the tissue generally produces unique alterations of the corresponding NIR (near infrared) reflectance spectrum in three primary bands of wavelengths (i.e., 1050-1350 nm, 1500-1800 nm, 2100-2300 nm) in which non-heme proteins (e.g., collagen and elastin), lipids, hemoglobin, and water absorb. Wavelength sets (e.g., two or more different wavelengths) may be chosen from one of the three primary wavelength bands based on the application (e.g., invasive or non-invasive) for the light source 22. It should be noted that, in accordance with present embodiments, the wavelength sets are chosen from within, and not from across the bands. Exemplary wavelength pairs may include $\lambda 1=1300$ nm, $\lambda 2=1168$ nm, and $\lambda 1=1230$ nm, $\lambda 2=1168$ nm. Exemplary techniques for wavelength selection and so forth may be found in U.S. Pat. No. 6,591,122, U.S. Publication No. 2003/0220548, U.S. Publication No. 2004/0230106, U.S. application Ser. No. 11/283,506 filed on Nov. 18, 2005, and U.S. application Ser. No. 11/282,947 filed on Nov. 18, 2005, which are incorporated herein by reference.

According to the results of numerical simulations and experimental studies, it is believed that the brain tissue water fraction can be measured in the presence of nonspecific scattering variation, temperature, and other interfering variables. For example, to ensure that measured reflectances and water content yield estimates of water fraction that are essentially insensitive to scattering variations, the lengths of the optical paths through the tissue and/or skull at the wavelengths at which the reflectances are measured may be substantially matched. This matching may be achieved by judicious selection of wavelength sets that have similar water absorption characteristics. Further, to ensure measured reflectances and water fractions yield estimates of water fractions that are essentially insensitive to temperature variations, the wavelengths at which reflectances are measured may be chosen to fit certain criteria. For example, in one embodiment the wavelength sets may be chosen to be close to temperature isobestic wavelengths in the water absorption spectrum. The wavelength pair of 1180 and 1300 nm are a pair of exemplary isobestic wavelengths in the water absorption spectrum. In another embodiment, the wavelength sets may be chosen such that the reflectances are combined in a way that cancels the temperature dependencies of the individual reflectances. Typically, absorption peaks of various biological tissue constituents may shift with variations in temperature. Thus, wavelengths may be selected at points in the absorption spectrum where no significant temperature shift occurs. In another embodiment, by knowing the value of this temperature shift, wavelength sets may be chosen such that temperature shift is mathematically canceled out when optical measurements are combined to compute the value of a tissue water metric.

Various constituents of brain tissue other than water may be included in a denominator of a ratio used to compute the tissue water fraction in accordance with present embodiments. The ratio may be represented as follows:

$$f_w = C_W / C_T,  \quad (\text{Eq. 1})$$

where $f_w$ is the fraction of water in the measured tissue, $C_w$ is the concentration of water in the measured tissue, and $C_T$ is the sum of tissue constituents over which the water fraction is being determined. As described below, $C_T$ may include all constituents of the tissue, in which case the total water fraction is determined. Alternatively $C_T$ may include all constituents except fat (lipid), in which case the lean water fraction is determined. In yet another alternative, $C_T$ may include all constituents except fat and bone, in which case the lean bone-free water fraction is determined. The term "concentration" as used above may refer to any number of standard means of expressing concentration. For example, concentration may reference a volume fraction.

Figure 2:
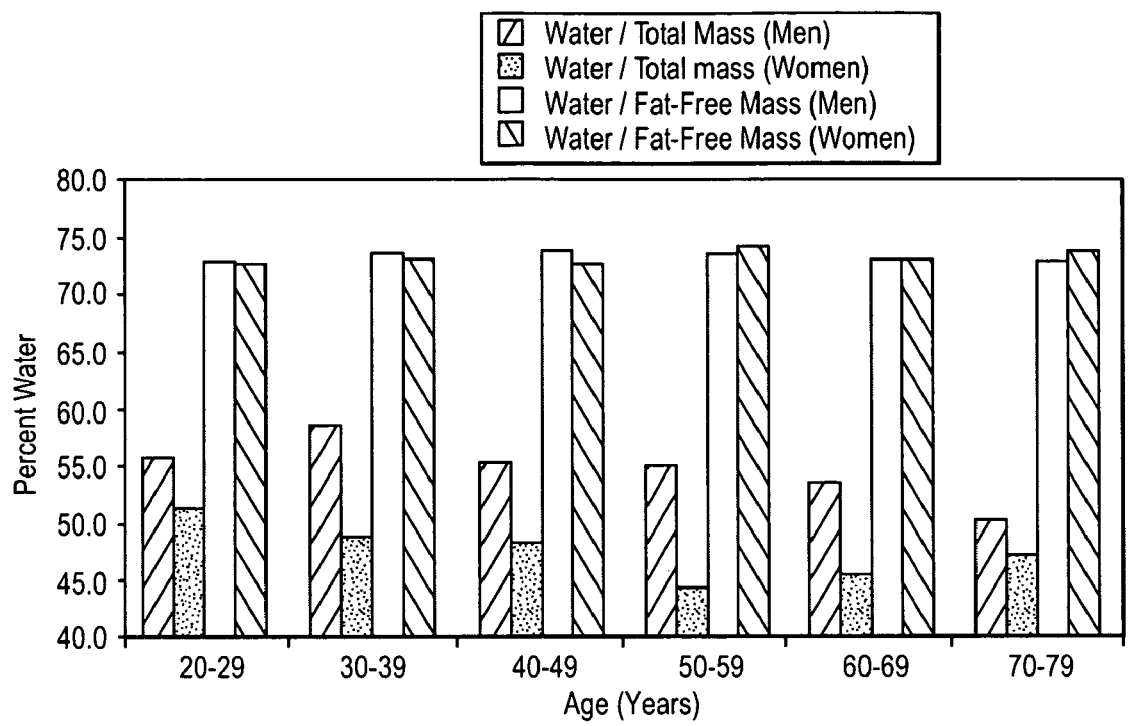
FIG. 2 is a bar graph that represents lean and total percent water measurements for various patient types, which supports a procedure in accordance with an exemplary embodiment of the present invention.

As indicated above, in one embodiment, all major tissue constituents (e.g., non-heme protein, lipid, and hemoglobin) are included in the denominator of the ratio. This may result in computation of a total tissue water fraction. However, when averaged across many patients, gender and age-related differences in fat content typically result in systematic variations in water content. This is illustrated in FIG. 2, which includes an exemplary graph of lean and total percent water measurements for various patient types. Accordingly, in one embodiment, certain constituents are specifically excluded from the measured tissue water fraction. Indeed, certain tissue constituents may be removed from the computation of tissue water fraction by selecting spectral regions where the absorbance contribution due to these tissue constituents is small, or by combining spectroscopic measurements made at multiple wavelengths to cancel the absorbance contribution due to these tissue constituents. Another method of excluding certain constituents from the computation of tissue water fraction is by controlling the measurement volume. This may be achieved in an exemplary embodiment through the geometric arrangement of the source and detector. For example, hemoglobin and/or lipid absorbance contributions may be excluded. The removal of the absorbance contribution due to lipid may be referred to as a lean hydration measurement and may result in what may be referred to as fractional water in fat-free or lean tissue. The lean hydration measurement may correlate to a fixed hydration index (e.g., 72%) for all well hydrated adults regardless of age, gender, body type, and so forth, as illustrated in FIG. 2. Accordingly, lean hydration measurement may be desirable for certain situations in accordance with present embodiments.

Figure 3:
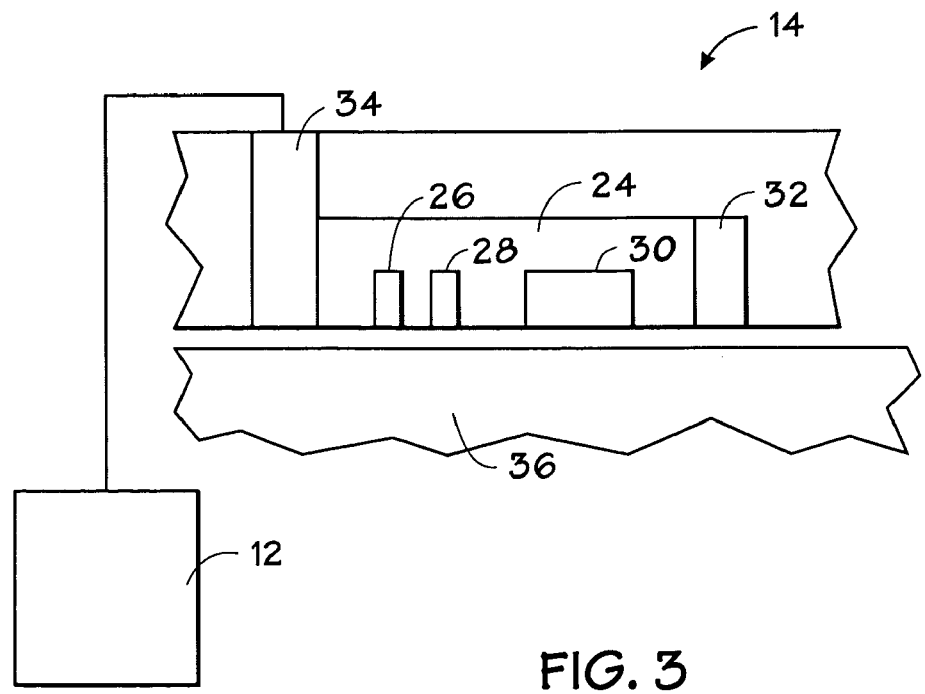
FIG. 3 is a block diagram of a sensor in accordance with an exemplary embodiment of the present invention.

FIG. 3 is a block diagram that is representative of a specific embodiment of the sensor 14 that operates in accordance with present embodiments. Specifically, as illustrated in FIG. 3, the sensor 14 may include a photospectrometry sensor or photo-sensor 24 that includes a first LED 26, a second LED 28, and a photo-detector 30. It should be noted that while the sensor 14, as illustrated in FIG. 3, merely includes two LEDs, in other embodiments the sensor 14 may include three or more LEDs or other wave emitting devices (e.g., superluminescent diodes (SLD), diode lasers, vertical cavity lasers (VCSELs), resonant cavity LEDs, tunable/scanning lasers, filament bulbs). The sensor 14 may also include a memory 32 and an interface 34 to store algorithms and facilitate communication with the monitor 12, respectively. The LEDs 26 and 28 receive drive signals from the monitor 12, which activates the LEDs 26 and 28 and causes them to emit signals (e.g., alternative emissions from each LED). The photo-sensor 24 is configured such that light from the activated LEDs 26 and 28 can pass into a patient's brain tissue 36 either directly or indirectly (e.g., via the skull). After being transmitted from or reflected from the brain tissue 36, the photo-detector 30 receives the dispersed light. The photo-detector 30 then converts the received light into a photocurrent signal, which is eventually provided to a signal-processing unit in the monitor 12. The monitor 12 may utilize data from the photocurrent signal to perform calculations relating to hydration of the brain tissue 36. For example, the monitor 12 may compare measured values with a table of established correlations of water content to determine a water content value for posting as the current brain tissue water fraction.

Figure 4:
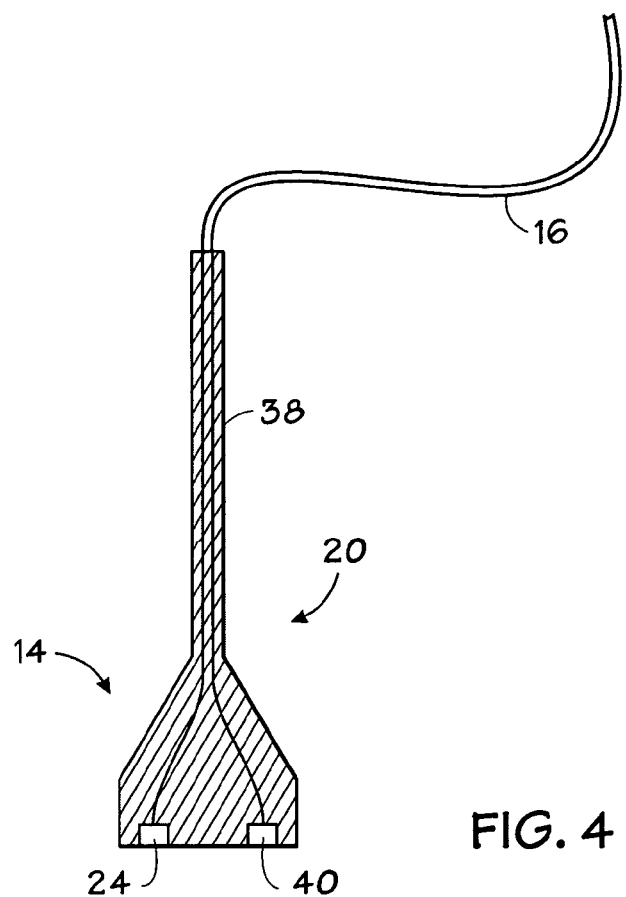
FIG. 4 is a cross-sectional, side view of an invasive sensor in accordance with an exemplary embodiment of the present invention.

As indicated above, embodiments of the present invention may be invasive or non-invasive. Accordingly, the sensor 14 may be configured for invasive operation, non-invasive operation, or both. In an invasive embodiment, the body 20 of the sensor 14 may include a shaft 38, as illustrated in FIG. 4. The shaft 38 may be configured to facilitate contact between the sensor 14 and brain tissue or to facilitate placement of the sensor 14 near the brain tissue. For example, the shaft 38 may comprise rigid or semi-rigid material that is approximately as long as typically required to reach brain tissue through the human skull (e.g., via a nasal cavity or an opening directly into the skull). Further, the body 20 for an invasive embodiment of the sensor 14 may be formed from a material that exhibits short-term or long-term biocompatibility to prevent undesired reactions when put in contact with living tissue. Additionally, the body 20 may be configured to protect internal components from exposure to elements (e.g., bodily fluids) that might interfere with the function of the internal components. It should be noted that the sensor 14 may be replaceable and disposable.

In one embodiment configured for invasive use, the sensor 14 may include the photo-sensor 24 and a pressure sensor 40 for measuring intracranial pressure, as illustrated in FIG. 4. The pressure sensor 40 and the photo-sensor 24 may both be integral to the sensor 14 and configured for placement inside a patient's head either in direct contact with brain tissue or very near brain tissue. In one embodiment, the sensor 14 may include the photo-sensor 24 and the pressure sensor 40 coupled to an intraventricular catheter (i.e., a catheter configured to be threaded into one of the lateral ventricles of the brain), a subarachnoid screw or bolt (e.g., a screw or bolt configured to be disposed through the skull in the space between the arachnoid and cerebral cortex), or the like. Further, the pressure sensor 40 may include an epidural sensor (e.g., a sensor configured to be disposed in the epidural space beneath the skull). Once inside the head, the pressure sensor 40 may sense the intracranial pressure and send measurements of the pressure to the monitor 12 via the cable 16. Inclusion of the pressure sensor 40 with the photo-sensor 24 may enable measurement of brain hydration in combination with intracranial pressure such that a perfusion (i.e., circulatory) status of the brain and a tissular hydration value of the brain can be assessed at the same time.

The photo-sensor 24 may be configured specifically for the invasive application. For example, in an invasive embodiment, the source-detector separation (i.e., the distance between LEDs 26 and 28, and photo-detector 30) and the spectral region of photo-emissions may be optimized for placement near or directly adjacent brain tissue. In one embodiment, the separation (i.e., source-detector separation) between the source (i.e., LEDs 26 and 28) and the detector (i.e., photo-detector 30) is approximately 2-3 mm and the spectral region is approximately 1500-1800 nm. In another embodiment, the source-detector separation is approximately 2-3 mm and the spectral region is approximately 2100-2300 nm. In yet another embodiment, the source-detector separation is approximately 1-5 mm and the spectral region is either 1500-1800 nm or 2100-2300 nm. In still another embodiment, the source-detector separation is approximately 0.1-5 mm and the spectral region is either 1500-1800 nm or 2100-2300 nm. Smaller source-detector separations allow for very shallow penetration depths for invasive applications. It should be noted that very short path lengths may be achieved in some embodiments by using fiber optics. For example, the source (e.g., LEDs 26 and 28) and/or detector (e.g., photo-detector 30) may be located in an external monitor and optical fiber may be used to transport the light to and/or from the tissue.

The exemplary values for the source-detector separation and the spectral region in invasive applications, as set forth above, facilitate factional water measurement in the brain tissue when the photo-sensor 24 is near or in contact with the brain tissue. Specifically, the spectral regions of 1500-1800 nm and 2100-2300 nm have shallow penetration into the tissue and clear distinctions between spectra for water, protein, and lipids. In other words, these spectral regions facilitate accurate measurement of tissue water content when the photo-sensor 24 is near or in contact with the brain tissue being monitored. Further, the source-detector separations of 2-3 mm, 1-5 mm, or 0.1-5 mm each selectively limit penetration depth. The larger the source-detector separation, the deeper the detected photo-emissions will have penetrated into the tissue. Similarly, the smaller the source-detector separation, the shallower the detected photo-emissions will have penetrated into the tissue. Accordingly, selection of a source-detector separation within one of these ranges may avoid overly shallow penetration and overly deep penetration, thus facilitating obtainment of measurements that are representative of actual brain tissue conditions.

Figure 5:
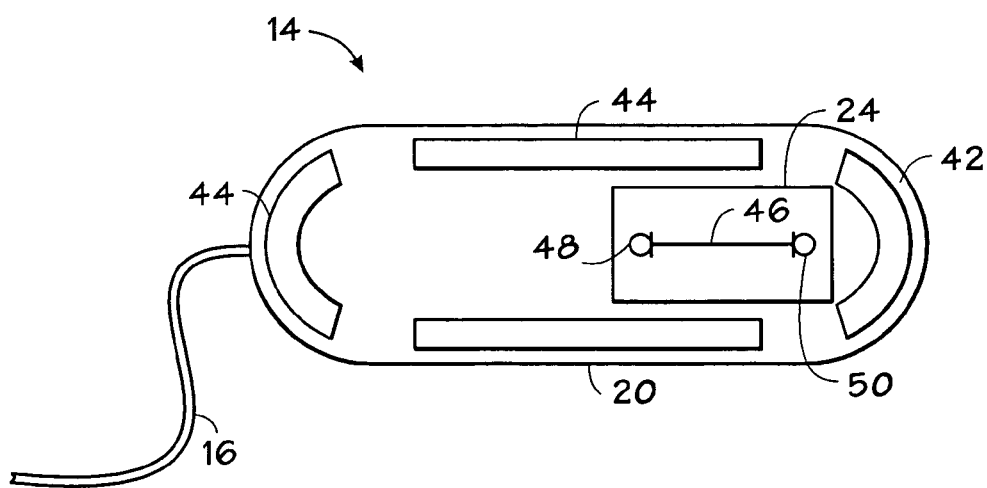
FIG. 5 is an attachment-side view of a non-invasive sensor in accordance with an exemplary embodiment of the present invention.

As set forth above, some embodiments of the present invention are non-invasive, which may be desirable to eliminate the need to physically penetrate the skull. In a non-invasive embodiment, the body 20 of the sensor 14 may be configured for placement adjacent a patient's forehead, as illustrated in FIG. 5. Specifically, FIG. 5 shows the attachment-side (i.e., the side configured to couple to the patient) of a non-invasive embodiment of the sensor 14. In this embodiment, the sensor body 20 may include a flexible sheet 42 that conforms and adheres to the patient's forehead. For example, the sheet 42 may comprise a thin, elongate piece of rubberized material, flexible plastic or woven fibers. The sheet 42 may include adhesive 44 disposed thereon to facilitate coupling to the patient. Additionally, the sensor 14 and/or the sensor body 20 may be disposable. Further, the body 20 for a non-invasive embodiment may be formed from a material that exhibits short-term or long-term biocompatibility to prevent undesired reactions when put in contact with the patient's skin. Additionally, the body 20 may be configured to protect internal components from exposure to elements (e.g., sweat) that might interfere with the function of the internal components.

As with the invasive embodiment, certain aspects of the sensor 14 may also be specifically optimized for the non-invasive application. In non-invasive embodiments, deep photon penetration (e.g., approximately 16 mm) is desirable to perform a brain hydration measurement through the skull without necessarily physically penetrating the skull. Accordingly, in some embodiments for non-invasive applications, the sensor 14 includes the photo-sensor 24 with a source-detector separation of at least 5 mm. Specifically, in some embodiments, the source-detector separation is approximately 10-30 mm. This source-detector separation is illustrated in FIG. 5 by the distance indicator 46, which is positioned between a source 48 (e.g., LEDs 26 and 28) and a detector 50. Additionally, the non-invasive embodiment may emit wavelengths in the 1050-1350 nm spectral region from the source 48. The 1050-1350 nm spectral region may be desirable for the non-invasive application because of its relatively weak absorption but distinctive spectra for water and other brain constituents (e.g., protein, lipids, carbohydrate, and salts). These characteristics of the 1050-1350 spectral region facilitate deep penetration (e.g., through the skull) into the brain tissue and clarity in the detected components (e.g., water and lipids). It should be noted that in some embodiments, a 900-1050 nm spectral region may be used for even greater penetration depths, with a correspondingly longer source-detector separation (1-30 cm). Water, lipid, and protein all have weak measurable absorbances in the 900-1050 nm region, given a long enough path length.

Figure 6:
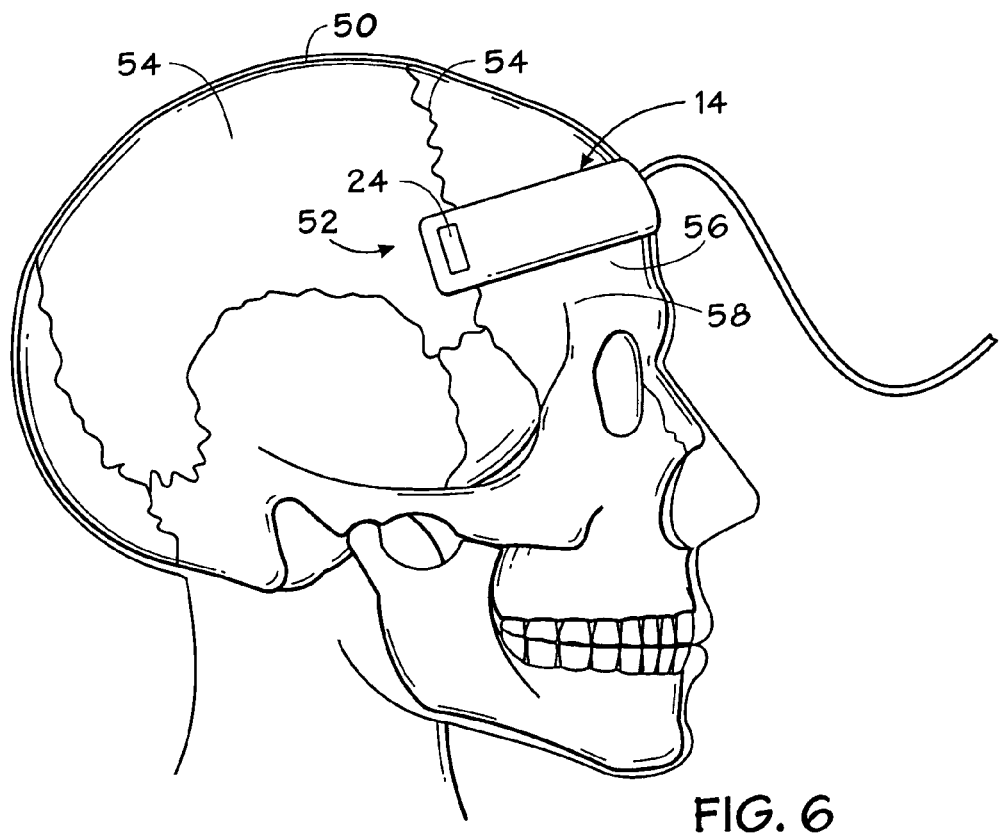
FIG. 6 is a side view of a sensor coupled to the skin around a patient's skull in accordance with an exemplary embodiment of the present invention.
Figure 7:
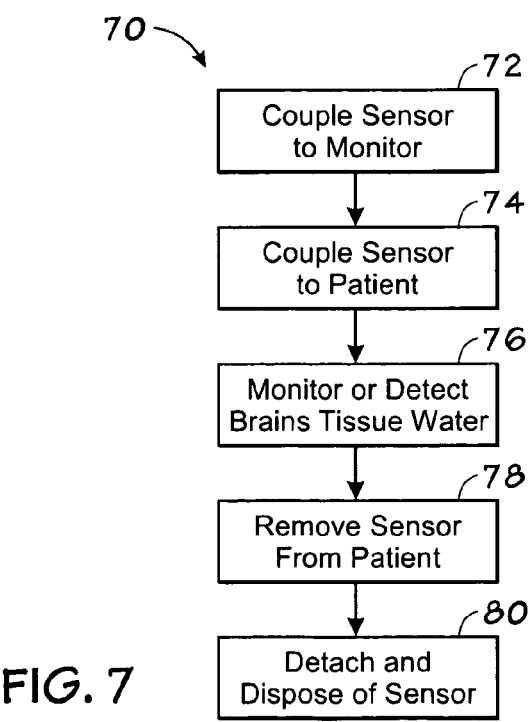
FIG. 7 is a block diagram of a method in accordance with an exemplary embodiment of the present invention.

FIG. 6 is a side view of the sensor 14 coupled to the skin around a patient's skull 50 in accordance with an exemplary embodiment of the present invention. Specifically, the illustrated sensor 14 is a non-invasive embodiment that includes the photo-sensor 24. The sensor 14 may be strapped or adhesively coupled to the skull 50. As illustrated in FIG. 7, when coupled to the patient, the photo-sensor 24 in the sensor 14 may be positioned on the partial bone region 52 of the skull 50, a slight distance (e.g., approximately 3 cm) behind the coronal suture 54. The coronal suture 54 may be defined as the suture between the parietal 54 and frontal bones 56 of the skull 50. This portion or region of the skull 50 does not substantially vary in thickness among groups. Indeed, among different racial (e.g., black and white) and gender groups of adults under 20 years of age, the variance in thickness of the skull 50 in the partial bone region 52 is less than other regions of the skull 50. Thus, attachment of the photo-sensor 24 in this region may facilitate consistent operation, consistent diagnosis, establishment and utilization of standardized data tables, and so forth. Other attachments sites for the sensor 14 may also be desirable in accordance with present embodiments. For example, other attachment sites for the photo-sensor 24 may include the frontal bone 56 or forehead and temporal region 58.

FIG. 7 is a block diagram of a method in accordance with an exemplary embodiment of the present invention. The method is generally designated by reference numeral 70. Block 72 represents attaching or coupling the sensor 14 to the monitor 12. Block 74 represents coupling the sensor to a patient. In a non-invasive embodiment, block 74 may include removably bonding the sensor 14 to the patients head with adhesive, as illustrated in FIG. 6. In an invasive embodiment, block 74 may include inserting the sensor 14 into a hole in the patient's skull until the sensor 14 contacts brain tissue or nearly contacts the brain tissue. In some embodiments, a scope may be utilized to guide the sensor 14 inside the skull (e.g., via nasal passage). Block 76 represents monitoring or detecting the water content in and around the brain tissue. The monitoring in block 76 may continue for any amount of time (e.g., an hour, a day, a week) depending on the condition of the patient. In order to avoid potential damage that may result from long-term placement, block 76 may include periodic removal and replacement of the sensor 14. Block 78 represents removal of the sensor 14 from the patient. Block 80 represents detachment of the sensor 14 from the patient, and disposal of the sensor 14.

While the invention may be susceptible to various modifications and alternative forms, specific embodiments have been shown by way of example in the drawings and will be described in detail herein. However, it should be understood that the invention is not intended to be limited to the particular forms disclosed. Rather, the invention is to cover all modifications, equivalents and alternatives falling within the spirit and scope of the invention as defined by the following appended claims.

What is claimed is:

1. A method of detecting or monitoring brain edema in a patient, comprising:

emitting a first light into the patient's brain tissue at a first wavelength through a partial bone region of the patient's skull, wherein the partial bone region of the patient's skull is approximately 3 cm behind a coronal suture of the patient's skull, wherein the coronal suture includes a suture between parietal and frontal bones of the patient's skull;

emitting a second light into the patient's brain tissue at a second wavelength through said partial bone region;

detecting the first and second lights after dispersion by the brain tissue at a detector; and determining an amount of water proximate the brain tissue based on the detected first and second lights.

2. The method of claim 1, comprising emitting a third light into the patient's brain tissue at a third wavelength.

3. The method of claim 2, comprising detecting the third light after reflection or dispersion by the brain tissue.

4. The method of claim 3, comprising determining the amount of water proximate the brain tissue based on the detected third light in combination with the detected first and second lights.

5. The method of claim 1, comprising emitting the first and second lights from at least approximately 5 mm away from the detector.

6. The method of claim 1, comprising emitting the first and second lights from approximately 10-30 mm away from the detector.

7. The method of claim 1, comprising emitting the first and second lights from approximately 1-5 mm away from the detector.

8. The method of claim 1, comprising penetrating approximately 16 mm into the patient with the first and second lights.

9. The method of claim 1, wherein the first and second wavelengths are within a 1050-1350 nm spectral region.

10. The method of claim 1, wherein the first and second wavelengths are within a 1500-1800 nm spectral region.

11. The method of claim 1, wherein the first and second wavelengths are within a 2100-2300 nm spectral region.

12. The method of claim 2, comprising emitting the third light into the brain tissue via the partial bone region.

13. A method of detecting or monitoring brain edema in a patient, comprising:

emitting a first light into the patient's brain tissue at a first wavelength approximately 1-5 mm away from a detector, wherein the first wavelength is within a 2100-2300 nm spectral region and wherein the first light is emitted through a partial bone region of the patient's skull approximately 3 cm behind a coronal suture of the patient's skull, wherein the coronal suture includes a suture between parietal and frontal bones of the patient's skull;

emitting a second light into the patient's brain tissue at a second wavelength approximately 1-5 mm away from the detector, wherein the second wavelength is within the 1500-2300 nm spectral region and wherein the second light is emitted through said partial bone region;

detecting the first and second lights after dispersion by the brain tissue at the detector; and determining an amount of water proximate the brain tissue based on the detected first and second lights.

14. The method of claim 13, comprising detecting a pressure within the patient's skull.

15. The method of claim 14, comprising determining a perfusion status and a tissular hydration value based on the pressure and the detection of the first and second lights.

16. A method of detecting or monitoring brain edema in a patient, comprising:

emitting a first light into the patient's brain tissue at a first wavelength approximately 10-30 mm away from a detector through a partial bone region of the patient's skull approximately 3 cm behind a coronal suture of the patient's skull, wherein the coronal suture includes a suture between parietal and frontal bones of the patient's skull, and wherein the first wavelength is within a 1050-1350 nm spectral region;

emitting a second light into the patient's brain tissue at a second wavelength approximately 10-30 mm away from the detector through said partial bone region, wherein the second wavelength is within the 1050-1350 nm spectral region;

detecting the first and second lights after dispersion by the brain tissue at the detector; and determining an amount of water proximate the brain tissue based on the detected first and second lights.

* * * * *